United States Patent [19]

Parent et al.

[11] Patent Number: 5,324,659
[45] Date of Patent: Jun. 28, 1994

[54] YEAST MUTANTS USEFUL FOR INDENTIFYING IMMUNOSUPRESSANTS

[75] Inventors: Stephen A. Parent, Cranbury, N.J.; Leonardo E. Brizuela, Heidelberg, Fed. Rep. of Germany; Gary L. Chrebet, Princeton; Keith A. Bostian, Westfield, both of N.J.

[73] Assignee: Merck & Co., Inc., Rahway, N.J.

[21] Appl. No.: 923,082

[22] Filed: Jul. 31, 1992

Related U.S. Application Data

[63] Continuation-in-part of Ser. No. 875,170, Apr. 28, 1992, abandoned, and a continuation-in-part of Ser. No. 696,661, May 7, 1991, abandoned, and a continuation-in-part of Ser. No. 703,970, May 22, 1991, abandoned, and a continuation-in-part of Ser. No. 703,967, May 22, 1991, abandoned, and a continuation-in-part of Ser. No. 703,964, May 22, 1991, abandoned.

[51] Int. Cl.$^5$ ............................................. C12N 1/16
[52] U.S. Cl. .................................. 435/255.2; 435/942
[58] Field of Search ........................ 435/255, 256, 942

[56] References Cited

PUBLICATIONS

Mol. & Collular Biol., vol. 11, No. 9, pp. 4616–4626 (Sep. 1991), by L. Brizuela, et al., entitled *Antifungal Properties of the Immunosuppressant FK-506: Identification of an FK-506-Responsive Yeast Gene Distinct from FKB1*.
Transplantation, vol. 47, No. 2, pp. 356-359 (Feb. 1989), by N. Yoshimura, et al., entitled *Effect of a New Immunosuppressive Agent, FK506, on Human Lymphocyte Responses In Vitro*.
Proc. Natl. Acad. Sci. USA, vol. 88, pp. 1948-1952 (1991) by Heitman, et al. (Cumulative).
Mol. & Cell. Biology (3/91), pp. 1718-1723 by Koltin, et al. (Cumulative).
J. Biol. Chem. 262:16871-16879 (1987) by Koltin, et al. (Cumulative).
Proc. Natl. Acad. Sci. USA 87:9231-9235 (1990), by Bierer, et al. (Cumulative).
Anal. Bioch. 72:248-254 (1976) by M. Bradford (Cumulative).
Eur. J. Appl. Microbiol. 3:125-133 (1976) by Dreyfuss, et al. (Cumulative).
J. Immunol. 144:251-258 (1990), by F. Dumont, et al. (Cumulative).
J. Immunol. 144:1418-1424 (1990), by F. Dumont, et al. (Cumulative).
Bio. Research on Indus. Yeasts, vol. III CRC Press, pp. 99-104 (1986), by Falco, et al. (Cumulative).
Can J. Chem. 58, 579-590 (1980) by Findlay, et al. (Cumulative).
Nature 337:476-478 (1989) by Fischer, et al. (Cumulative).
Gene 83:39-46 (1989), by Haendler, et al. (Cumulative).
Science 226:544-547 (1984), by Handschumacher, et al. (Cumulative).

(List continued on next page.)

*Primary Examiner*—Marian C. Knode
*Attorney, Agent, or Firm*—J. Eric Thies; Robert J. North; Charles M. Caruso

[57] ABSTRACT

Disclosed is a process utilizing yeast mutants for identifying active FK-506 type immunosuppressants. The process utilizes *Saccharomyces cerevisiae* mutants containing an fkr1, fkr2, fkr3 mutant gene or mixture thereof, which are resistant to FK-506 but sensitive to rapamycin. These mutants can be used in a diagnostic procedure for identifying FK-506 and FK-506 type immunosuppressants and in screening assays for compounds and fermentation broths which exhibit FK-506 type immunosuppressive activity. Specifically disclosed are the new yeast mutants, *Saccharomyces cerevisiae* YKF093, (Merck Culture Collection No. MY 2088) ATCC No. 74055, containing an fkr3 mutant gene, *Saccharomyces cerevisiae* YKF 012, (Merck Culture Collection No. MY 2096) ATCC No. 74061, which contains an fkr1 mutant gene, *Saccharomyces cerevisiae* YFK 014, (Merck Culture Collection No. MY 2097) ATCC No. 74062 and YFK-023-17A (Merck Culture Collection No. MY 2098) ATCC No. 74063, both which contain an fkr2 mutant gene and are useful in identifying active FK-506 type immunosuppressants.

1 Claim, 5 Drawing Sheets

OTHER PUBLICATIONS

Nature 341:758–760 (1989), by Harding, et al. (Cumulative).
J. Lab. Clin. Med. 72:511–516 (1968) by Harwick, et al. (Cumulative).
J. Antibiotics 40:1249–1255 (1987) by Kino, et al. (Cumulative).
J. Antibiotics 40:1256–1265 (1987) by Kino, et al. (Cumulative).
J. Immunol. 137:1054–1059 (1986) by Koletsky, et al. (Cumulative).
Proc. Natl. Acad. Sci. USA 81:5214–5218 (1984), by Kronke, et al. (Cumulative).
Nature 329:268–270 (1987), by Lang, et al. (Cumulative).
Genetics 125:13–20 (1990), by Leppert, et al. (Cumulative).
Can. J. Physiol. Pharmacol. 55:48–51 (1977), by Martel, et al. (Cumulative).
Transplantation 49:798–802 (1990) by Metcalfe, et al. (Cumulative).
Enzymology, vol. 101 pp. 202–211 (1983), by Rothstein (Cumulative).
Can. J. Genet. Cytol. 24:493–503 (1982) by Saunders, et al. (Cumulative).
J. Immunol. 139:1797–1803 (1987) by Sawada, et al. (Cumulative).
Proc. Natl. Acad. Sci. USA 86:5390–5394 (1989) by Schneuwly, et al. (Cumulative).
Lab. Course Manual for Methods in Yeast Genetics (1986) by Sherman, et al. (Cumulative).
Ann. Rev. Immunol., vol. 3, pp. 397–423 (1985), by Shevach (Cumulative).
Nature 338:67–70 (1989), by Shieh, et al. (Cumulative).
J. Immunol. 143:1580–1583 (1989), by Siekierka, et al. (Cumulative).
Nature 341:755–757 (1989), by Siekierka, et al. (Cumulative).
J. Biol. Chem. 265:21011–21015 (1990), by Siekierka, et al. (Cumulative).
Bioch. Pharmacol, 40:2201–2208 (1990) by Sigal, et al. (Cumulative).
Genetics 122:19–27 (1989), by Sikorski, et al. (Cumulative).
J. Mol. Biol. 153:305–321 (1981), by Sprague, Jr., et al. (Cumulative).
Lancet 2:1000–1004 (1989) by Starzl, et al. (Cumulative).
Curr. Gent. 10:665–670 (1986) by Subid, et al. (Cumulative).
Nature 337:473–475 (1989) by Takahashi, et al. (Cumulative).
Transp. Proceed. 19:11–16 (1987) by Tanaka, et al. (Cumulative).
Immunol. Today 10:6–9 (1989) by Thomson (Cumulative).
Immunol. Today 11:35–36 (1990) Thomson (Cumulative).
J. Immunol. 143:718–726 (1989), by Tocci, et al. (Cumulative).
J. Biol. Chem. 263:14433–14440 (1988), by Tropschug, et al. (Cumulative).
Nature 342:953–955 (1989) by Tropschug, et al. (Cumulative).
Nature 346:674–677 (1990), by Tropschug, et al. (Cumulative).
J. Antibiot. 28:721–726 (1975), by Vezina, et al. (Cumulative).
Proc. Natl. Acad. Sci. USA (1991), by Wiederrecht, et al. (Cumulative).
Transplantation 47:356–359 (1989), by Yoshimura, et al. (Cumulative).
Mol. and Cell. Biol., Sep. 1991, pp. 4616–4626, by Brizuela, et al. (Cumulative).

YEAST MUTANTS USEFUL FOR INDENTIFYING IMMUNOSUPRESSANTS

CROSS REFERENCES TO RELATED APPLICATIONS

The present case is a combined continuation-in-part application of Ser. No. 07/875,170 filed Apr. 28, 1992 now abandoned; Ser. No. 07/696,661 filed May 7, 1991 now abandoned; Ser. No. 07/703,970 filed May 22, 1991 now abandoned; Ser. No. 07/703,967 filed May 22, 1991 now abandoned; and Ser. No. 07/703,964 filed May 22, 1991 now abandoned.

BACKGROUND OF THE INVENTION

1. Field of the Invention

This invention relates to a new process utilizing new yeast mutants for identifying active FK-506 type immunosuppressants. Specifically disclosed are the new yeast mutants, *Saccharomyces cerevisiae* YFK093, (Merck Culture Collection No. MY 2088) ATCC No. 74055, containing an fkr3 mutant gene, *Saccharomyces cerevisiae* YFK 012, (Merck Culture Collection No. MY 2096) ATCC No. 74061, which contains an fkr1 mutant gene, *Saccharomyces cerevisiae YFK* 014, (Merck Culture Collection No. MY 2097) ATCC No. 74062 and YFK-023-17A (Merck Culture Collection No. MY 2098) ATCC No. 74063, both which contain an fkr2 mutant gene.

2. Brief Description of Disclosures in the Art

In 1983, the US FDA approved cyclosporin, an extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, now issued as U.S. Pat. No. 4,894,366 hereby incorporated by reference, describes a new macrolide immunosuppressant FK-506 which is reputed to be 100 times more effective than cyclosporin. The macrolide is produced by fermentation of a particular strain of *Streptomyces tsukubaensis*. Also described is the closely related macrolide immunosuppressant FK-520, (FK-900520) produced by *S. hygroscopicus* subsp. *yakushimaensis*.

In the synthesis of new FK-506 type immunosuppressant analogs, it would be helpful to have a single, convenient diagnostic assay, not involving laboratory animals, to distinguish between those analogs of FK-506 which are agonists and those which are antagonists, i.e. rapamycin. Further, it would be helpful to have a single convenient diagnostic assay to establish the presence of FK-506 type immunosuppressant type activity in a fermentation broth, as opposed to other immunosuppressants; i.e. rapamycin.

Other strains of *Saccharomyces cerevisiae* and *Nerosspora crassa* are described in Nature, Vol. 342, pp. 953–955, which are resistant to cyclosporin A and lack detectable cyclophilin binding activity.

However, no description of mutant *S. cerevisiae* strains which are FK-506 resistant and growth dependent at 37° C., are described in the literature to date.

SUMMARY OF THE INVENTION

Figure 1:
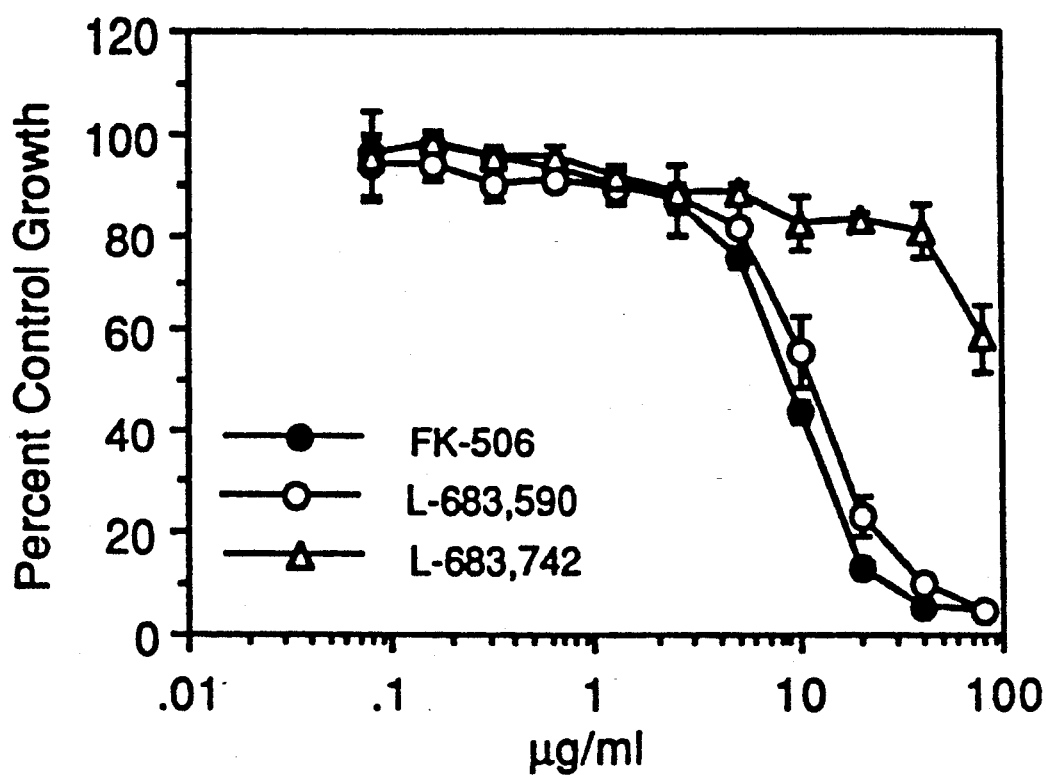
FIG. 1 illustrates the ability of FK-506 analogues to inhibit vegetative yeast growth in a dose-dependent manner. The ability of FK-506, L-683,590, (FR-900520) and L-683,742 to inhibit the vegetative growth of strain YFK005 was assayed in liquid culture, and the results are presented as the percent of control growth in the absence of antibiotic.

By this invention there is provided a biologically pure culture of a new *Saccharomyces cerevisiae* yeast mutant containing an fkr 3 mutant gene, and specifically, *Saccharomyces cerevisiae* YFK093, (MY 2088) ATCC No. 74055, which can be cultured at 30° C., but requires FK-506 or FR-900520 for culturing at 37° C. A process for isolating this mutant and other fkr3 mutants is also provided.

Also provided is a process for testing a compound or fermentation broth for FK-506 immunosuppressant-type activity comprising the steps of; (a) contacting said compound or broth with a *Saccharomyces cerevisiae* mutant containing an fkr3 mutant gene at 37° C., and (2) observing the growth characteristics of said mutant, which are positive in the presence of FK-506 immunosuppressive-type activity.

Further provided is a biologically pure form of a *Saccharomyces cerevisiae* mutant containing an fkr2 mutant gene, said mutant exhibiting observable growth characteristics at 30° C. in a growth medium containing FK-506 but not in the presence of rapamycin.

Furthermore, provided are biologically pure cultures of new yeast mutants, *Saccharomyces cerevisiae* YFK 014, (MY 2097) ATCC No. 74062 and YFK-023-17A (MY 2098), ATCC No. 74063, which contain an fkr2 mutant gene and are resistant to KF-506 or FR-900520 but sensitive to rapamycin. A process for isolating these mutants and other fkr2 mutants is also provided.

Further provided is a biologically pure form of a *Saccharomyces cerevisiae* mutant containing an fkr1 mutant gene, said mutant exhibiting observable growth characteristics at 30° C. in a growth medium containing FK-506 but not in the presence of rapamycin.

In addition, there is provided a biologically pure culture of new yeast mutant, *Saccharomyces cerevisiae* YFK 012, (MY 2096) ATCC No. 74061, which contains an fkr1 mutant gene and is sensitive to rapamycin but resistant to FK-506 or FK-900520. A process for isolating this mutant and other fkr1 mutants is also provided.

Furthermore, there is provided a process to identify FK-506 or an FK-506 type immunosuppressant comprising the step of culturing a *Saccharomyces cerevisiae* mutant containing an fkr1, fkr2 or fkr3 mutant gene or mixture thereof, in the presence of an FK-506 type immunosuppressant. These mutants grow in the presence of FK-506 at 20°-35° C., preferably 30° C. and not in the presence of rapamycin while their wild-type parents are unable to grow in the presence of either KF-506 or rapamycin

DETAILED DESCRIPTION OF THE INVENTION AND PREFERRED EMBODIMENTS

The present invention involves the culturing of different *Saccharomyces cerevisiae* mutants.

The microorganisms are currently on deposit with the American Type Culture Collection, 12301 Parklawn Drive in Rockville, Md. as indicated by the herein described ATCC Nos. The biological characteristics for each microorganism are briefly described herein below. The recommended storage conditions are to store in the frozen state atv-80° C.; for test, to maintain at 28° C. on YPAD medium containing: yeast extract, 10 g; bacto peptone, 20 g; dextrose, 20 g; and adenine, 60 mg/L.

In the following text, the numbers in parentheses refer to specific references listed in the Reference Section in the back of the specification.

Based upon these following data, the microorganisms are identified as members of the yeast genus Saccharomyces.

The following are general descriptions of the *Saccharomyces cerevisiae* mutants, the first being strain YFK 093, ATCC No. 74055, (fkr3).

YFK 093—Observations of growth, general cultural characteristics and carbon source utilization were made in accordance with the methods of Shirling and Gottleib (International *J. System, Bacteriol.* 16:313-340). Coloration of the culture was determined by comparison with color standards contained in the Inter-Society Color Council-National Bureau of Standards Centroid Color Charts (U.S. Dept of Commerce National Bureau of Standards supplement to NBS Circular 553, 1985).

*Saccharomyces cerevisiae* YFK 093, MY 2088—Growth occurs at 27° C. on yeast malt extract agar, Sabouraud's maltose agar, and trypticase soy agar, as well as on Sabouraud's dextrose agar at 27° and 37° C. (Note: growth occurs at 37° C. attendant with heavy streaking, but observable growth is inhibited with very light streaking of the agar plates). Culture is mature in 72 hours. Colonies are white to cream colored, smooth, entire, butryous, and fragrant. Cells are globose, subglobose, to ovoid 4.5-7 µm in diameter. Pseudohyphae development was not observed. Reproduction is by multilateral budding and ovoid ascospores 9-12×8-.5-11 µm. Vegetative cells are gram positive, whereas ascopospores are gram negative. A characterization using the API 20C clinical yeast system was undertaken to determine the ability of the organism to utilize various carbon sources for growth. Results obtained were negative as the strain is an auxotroph which requires adenine, leucine, lysine, tryptophan, and uracil for growth.

The following is a general description of *Saccharomyces cerevisiae* strain YFK 005, (MY 2094) ATCC No. 74059, the parental strain for fkr1 and fkr2 mutants.

YFK 005—Observations of growth, general cultural characteristics and carbon source utilization were made in accordance with the methods of Shirling and Gottleib (International *J. System Bacteriol.* 16:313-340). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

*Saccharomyces cerevisiae* YFK 005, MY 2094—Growth occurs at 27° C. on yeast malt extract agar, trypticase soy agar, malt extract agar, and corn meal agar, as well as on Sabouraud's dextrose agar at 27° C. and 37° C. Culture is mature in 72 hours. Colonies are pale to cream colored, slightly raised to convex, smooth, butyryous, and fragrant. Cells are globose, subglobose, to ovoid, cylindrical 3.8-11×3.8-5.7 µm. Reproduction is by multilateral budding, and globose ascospores (1-4 per ascus). Asci are globose 9.5-11.4 µm in diameter. Pseudohyphae development seen on malt extract agar and corn meal agar. Ascospores are gram negative, whereas vegetative cells are gram positive.

The following is a general description of *Saccharomyces cerevisiae* strain YFK 007, (MY 2095) ATCC No. 74060, the parental strain for fkr3 mutants.

YFK 007—Observations of growth, general cultural characteristics and carbon source utilization were made in accordance with the methods of Shirling and Gottleib (International *J. System, Bacteriol.* 16:313-340). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

*Saccharomyces cerevisiae* YFK 007, MY2095—Growth occurs at 27° C. on yeast malt extract agar, trypticase soy agar, malt extract agar, and corn meal agar, as well as on Sabouraud's dextrose agar at 27° C. and 37° C. Culture is mature in 72 hours. Colonies are pale to. cream colored, slightly raised to convex, smooth, butyryous, and fragrant. Cells are globose, subglobose, to ovoid, cylindrical 3.8–9.5×3.8–5.7 mm. Reproduction is by multilateral budding, and globose ascospores (1–4 per ascus). Asci are globose 9.5–11.4 mm in diameter. Pseudohyphae development seen on malt extract agar and corn meal agar. Ascospores are gram negative, whereas vegetative cells are gram positive.

The following is a general description of *Saccharomyces cerevisiae* strain YFK 012, (MY 2096) ATCC No. 74061, an fkr1 mutant produced from YFK 005.

YFK 012—Observations of growth, general cultural characteristics and carbon source utilization were made in accordance with the methods of Shirling and Gottleib (International *J. System, Bacteriol.* 16:313–340). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

*Saccharomyces cerevisiae* YFK 012, MY 2096— Growth occurs at 27° C. on yeast malt extract agar, trypticase soy agar, malt extract agar, and corn meal agar, as well as on Sabouraud's dextrose agar at 27° C. and 37° C. Culture is mature in 72 hours. Colonies are pale to cream colored, slightly raised to convex, smooth, butyryous, and fragrant. Cells are globose, subglobose, to ovoid, cylindrical 3.8–9.5×3.8–5.7 mm. Reproduction is by multilateral budding, and globose ascospores (1–4 per ascus). Asci are globose 9.5–11.4 mm in diameter. Pseudohyphae development seen on malt extract agar and corn meal agar. Ascospores are gram negative, whereas vegetative cells are gram positive.

The following is a general description of *Saccharomyces cerevisiae* strain YFK 014, (MY 2097) ATCC No. 74062, an fkr2 mutant produced from YFK 005.

YFK 014—Observations of growth, general cultural characteristics and carbon source utilization were made in accordance with the methods of Shirling and Gottleib (International *J. System, Bacteriol.* 16:313–340). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

*Saccharomyces cerevisiae* YFK 014, MY 2097— Growth occurs at 27° C. on yeast malt extract agar, trypticase soy agar, malt extract agar, and corn meal agar, as well as on Sabouraud's dextrose agar at 27° C. and 37° C. Culture is mature in 72 hours. Colonies are pale to cream colored, slightly raised to convex, smooth, butyryous, and fragrant. Cells are globose, subglobose, to ovoid, cylindrical 3.8–8.5×3.8–5.7 mm. Reproduction is by multilateral budding, and globose ascospores (1–4 per ascus). Asci are globose 9.5–11.4 mm in diameter. Pseudohyphae development seen on malt extract agar and corn meal agar. Ascospores are gram negative, whereas vegetative cells are gram positive.

The following is a general description of *Saccharomyces cerevisiae* strain YFK 023-17A (MY 2098) ATCC No. 74063, an fkr2 strain derived from YFK 014 by a genetic cross with YFK 007.

YFK 023-17A—Observations of growth, general cultural characteristics and carbon source utilization were made in accordance with the methods of Shirling and Gottleib (International *J. System, Bacteriol.* 16:313–340). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

*Saccharomyces cerevisiae* YFK 023-17A MY 2098— Growth occurs at 27° C. on yeast malt extract agar, trypticase soy agar, malt extract agar, and corn meal agar, as well as on Sabouraud's dextrose agar at 27° C. and 37° C. Culture is mature in 72 hours. Colonies are pale to cream colored, slightly raised to convex, smooth, butyryous, and fragrant. Cells are globose, subglobose, to ovoid, cylindrical 3.8–7.6×3.8–5.7 mm. Reproduction is by multilateral budding, and globose ascospores (1–4 per ascus). Asci are globose 9.5–11.4 mm in diameter. Pseudohyphae development seen on malt extract agar and corn meal agar. Ascospores are gram negative, whereas vegetative cells are gram positive.

The present invention also involves the culturing of the above-described *Saccharomyces cerevisiae* FK-506 resistant mutants and their parental strains YFK005 and YFK007: YFK 005, MY 2094, ATCC No. 74059; YFK 007, MY 2095, ATCC No. 74060; YFK 012, MY 2096, ATCC No. 74061; YFK 014, MY 2097, ATCC No. 74062; YFK 023-17A, MY 2098, ATCC No. 74063.

FK-506 is a novel and potent antagonist of T cell activation and an inhibitor of fungal growth. Its immunosuppressive activity can be antagonized by the structurally related antibiotic rapamycin, and both compounds interact with cytoplasmic FK-506 binding proteins (FKBPs) in T cells and yeast. In this disclosure, we show that FK-506 and two analogs inhibit vegetative growth of *Saccharomyces cerevisiae* in a fashion that parallels the immunosuppressive activity of these compounds. Yeast mutants resistant to FK-506 were isolated, defining at least three complementation groups (fkr1–3). These fkr mutants shown no alteration in their levels of FK-506 binding activity (FKBP). Likewise, strains carrying null alleles of FKB1 (the yeast gene coding for the FK-506 binding protein) remain FK-506 sensitive, indicating that depletion of yFKBP is not sufficient to confer an FK-506 resistance phenotype, although fkb1 null mutants are resistant to rapamycin. FKB1 does not map to the three fkr loci defined here. These results suggest that yFKBP mediates the inhibitory effect of rapamycin, but at least one other protein is directly involved in mediating the activity of FK-506 . Interestingly, the ability of FK-506 to rescue a temperature sensitive growth defect of the fkr3 mutant suggests that the FKR3 gene might define such a protein.

FK-506, cyclosporia A (CsA), and rapamycin are natural products which posses potent immunosuppressive activities in vitro and in vivo. CsA has been the primary drug used clinically to prevent the rejection of transplanted organs and bone marrow, as well as for the treatment of selected autoimmune diseases (31). (Please note that references are referred to in parentheses, and a listing of the numbered references is given in the back of the specification.) This cyclic undecapeptide inhibits an early step in T cell activation, and prevents transcription of several lymphokine genes responsible for promoting T cell growth and differentiation (20). Despite dramatic structural differences, the macrolide FK-506 elicits similar effects on the immune system. However, the concentrations at which FK-506 suppresses T cell activation (17,18,28) and lymphokine expression (45,51) are 10–100 fold lower than that of CsA. This has prompted clinical evaluation of FK-506 for use in organ transplantation (39,44).

FK-506 and CsA bind to the distinct cytosolic binding proteins FKBP (15,33,34) and cyclophilin (14), respectively. Both of these binding proteins are ubiquitous, abundant and highly conserved phylogenetically (13,19,35). They also possess peptidyl-prolyl cis-trans isomerase (PPIase) activities which can be specifically inhibited by their respective ligands at concentrations relevant to immunosuppression (12,15, 34,41). PPIase activity accelerates the slow refolding of proteins and peptides in vitro (21), and is believed to play a role in folding these substrates into their native conformations in vivo. Support for such a role is provided by the finding that the Drosophila ninaA gene encodes a cyclophilin homolog which affects rhodopsin expression post-translationally (29,32). However, definitive roles of the binding proteins or their catalytic activities in T cell activation have not been presented. Moreover, both binding proteins are present at high intracellular concentrations which are unlikely to be saturated by therapeutic levels of FK-506 of CsA. The immunosuppressive activities of these antibiotics may also be mediated by other less abundant cellular proteins with higher affinities for FK-506 or CsA.

Rapamycin (see U.S. Pat. No. 3,929,992) is chemically related to FK-506 (11,23), but despite its structural similarity, its immunosuppressive properties are distinct. In contrast to FK-506, rapamycin impairs the response of T cells to the interleukin IL-2 rather than inhibiting IL-2 expression (7). In addition, FK-506 and rapamycin, but not CsA, antagonize each other's immunosuppressive properties, suggesting that they share a common receptor molecule(s) (8). Their antagonistic properties have been confirmed and extended by the discovery that rapamycin antagonizes FK-506 inhibition of other T lymphocyte events which are sensitive to FK-506 (2). Furthermore, both antibiotics bind to recombinant human FKBP with similar affinities and inhibit the receptor's isomerase activity, as measured in vitro (2), suggesting that PPIase inhibition is insufficient to explain the immunosuppressive activity of these antibiotics.

All three immunosuppressants also possess antifungal activities (6,17,49), and CsA and rapamycin were first discovered as antifungal agents. Moreover, fungal homologs of cyclophilin (13,19,46) and FKBP (35,48) have been identified. CsA resistant mutants of *Saccharomyces cerevisiae* and *Neurospora crassa* either lack cyclophilin, or contain a receptor which fails to bind CsA, indicating that cyclophilin mediates CsA cytotoxicity in these organisms (47). These results also suggest that antibiotic cytotoxicity results from a cyclophilin-CsA complex. Yeast FKBP is remarkably similar to its mammalian counterpart in several important aspects (35); it is an abundant protein which binds FK-506 and possesses PPIase activity. It also shares significant amino acid sequence conservation with mammalian FKBPs. Like cyclophilin, the yeast FKBP gene, FKB1 is single copy and nonessential, but its role in the action of FK-506 on yeast is unknown (50).

These observations prompted us to investigate the nature of FK-506's antifungal activity and to determine whether it is mechanistically related to the antibiotic's immunosuppressive properties. Our approach has been to genetically define the cellular targets involved in mediation of FK-506 activity in yeast, and to determine the role of yeast FLBP in this process. We demonstrate here that FK-506 analogues, representing a 6-fold range of immunosuppressive activity inhibit yeast growth in a manner that parallel their relative immunosuppressive activities. We also describe a process for the isolation of recessive, co-dominant and dominant FK-506 resistant mutants (fkr). The recessive and co-dominant mutants fall into three complementations groups, which we have names fkr1, fkr2 and fkr3. These mutants are not the result of typical pleiotropic drug resistance mutations, and their levels of FK-506 binding activity are unaffected. The genes defined by the fkr mutants do not map to FKB1, and fkb1 null mutants lacking FK-506 binding activity are FK-506 sensitive, although they become resistant to rapamycin. Based on these results, we reasonably believe that rapamycin's cytotoxicity is mediated through yFKBP and other protein(s) are present which modulate the activity of FK-506. Lastly, we present results suggesting that the FKR3 gene probably encodes such a protein, based upon the fkr3 mutant's responses to FK-506.

TABLE I

*S. cerevisiae* strains

| Strain | Genotype | Source |
| --- | --- | --- |
| YFK001 | MATa ade his3-11, 15 leu2-3, 112 ura 3-52 | Sc347 |
| YFK003 | MATa ade2-101 lys2-801 trp1-D1 ura3-52 | YPH1 |
| YFK005 | MAT alpha ade2-101 his3-D200 lys2-801 trp1-D1 ura3-52 | YPH54 (starting strain for fkr1, fkr2) |
| YFK007 | MATa ade2-101 leu2-D1 lys2-801 trp1-D1 ura3-52 | YPH98 (starting strain for fkr3) |
| YFK009 | Mat alpha ade2-1 can1-100 his3-11, 15 leu2-3, 112 trp1-1 ura3-1 | W303-1B |
| YFK012 | MAT alpha ade2-101 his3-D200 lys2-801 trp1-D1 ura3-52 fkr1 | This study |
| YFK014 | MAT alpha ade2-101 his3-D200 lys2-801 trp1-D1 ura3-52 fkr2 | This study |
| YFK045 | MAT alpha ade2-101 his3-D200 lys2-801 trp1-D1 ura3-52 fkr1 | This study |
| YFK054 | MAT alpha ade2-101 his3-D200 lys2-801 trp1-D1 ura3-52 fkr1 | This study |
| YFK093 | MATa ade2-101 leu2-D1 lys2-801 trp1-D1 ura3-52 fkr3 | This study |
| YFK021-5C | MATa ade2-101 leu2-D1 lys2-801 trp1-D1 ura3-52 fkr1 | This study |
| YFK023-2A | MAT alpha ade2-101 his3-D200 lys2-801 trp1-D1 ura3-52 fkr2 | This study |
| YFK023-2B | MATa ade2-101 leu2-D1 lys2-801 trp1-D1 ura3-52 fkr2 | This study |
| YFK023-3B | MATa ade2-101 leu2-D1 lys2-801 trp1-D1 ura3-52 fkr2 | This study |
| YFK023-17A | MATa ade2-101 leu2-D1 lys2-801 trp1-D1 ura3-52 fkr2 | This study |
| YFK059-8B | MATa ade2-101 leu2-D1 lys2-801 trp1-D1 ura3-52 fkr1 | This study |
| YFK115 | MATa SUC2 mal mel gal2 CUP1 | S288C from Yeast Genetics Stock Center (Berkeley, Ca). |
| YFK164-1D | MAT alpha ade2-101 his3-D200 lys2-801 trp1-D1 ura3-52 fkb1-1::URA3 | This study |
| YFK186 | MATa ade2 his4 leu2 lys2 trp1 tyr1 ura3 SUP4-3 cyh2 bar1-1 | DJ211.5.3 |
| YFK187 | MAT alpha ade2-101 his3-D200 lys2-801 trp1-D1 ura3-52 fkb1-2::URA3 | This study |

TABLE I-continued

S. cerevisiae strains

| Strain | Genotype | Source |
|---|---|---|
| YFK188 | MATa ade2-101 leu2-D1 lys2-801 trp1-D1 ura3-52 fkb1-2::URA3 | This study |

Auxotrophic markers ade2-101 and lys2-801 are ochre and amber suppressible, respectively.

TABLE II

Tetrad analysis of crosses between various fkr strains

| | | | No. of tetrads FK-506$^R$: FK-506$^S$ | | | | |
|---|---|---|---|---|---|---|---|
| Cross$^a$ | Parents | Relevant Genotype$^b$ | 4:0 | 3:1 | 2:2 | 1:3 | 0:4 |
| YFK016 | YFK005 x YFK007 | FKR/FKR | 0 | 0 | 0 | 0 | 34 |
| YFK021 | YFK007 x YFK012 | FKR1/fkr1 | 0 | 0 | 24 | 1 | 0 |
| YFK059 | YFK007 x YFK054 | FKR1/fkr1 | 0 | 0 | 29 | 0 | 0 |
| YFK023 | YFK007 x YFK014 | FKR2/fkr2 | 0 | 13 | 17 | 0 | 0 |
| YFK200 | YFK007 x YFK023-2A | FKR2/fkr2 | 0 | 0 | 6 | 0 | 0 |
| YFK116 | YFK005 x YFK093 | FKR3/fkr3 | 0 | 0 | 25 | 0 | 0 |
| YFK189 | YFK012 x YFK021-5C | fkr1/fkr1 | 9 | 0 | 0 | 0 | 0 |
| YFK190 | YFK045 x YFK021-5C | fkr1/fkr1 | 22 | 0 | 0 | 0 | 0 |
| YFK191 | YFK045 x YFK059-8B | fkr1/fkr1 | 18 | 0 | 0 | 0 | 0 |
| YFK192 | YFK054 x YFK021-5C | fkr1/fkr1 | 6 | 0 | 0 | 0 | 0 |
| YFK193 | YFK014 x YFK023-2B | fkr2/fkr2 | 6 | 0 | 0 | 0 | 0 |
| YFK195 | YFK012 x YFK023-2B | FKR1/fkr1 FKR2/fkr2 | 1 | 5 | 0 | 0 | 0 |
| YFK196 | YFK054 x YFK023-2B | FKR1/fkr1 FKR2/fkr2 | 0 | 3 | 1 | 0 | 0 |
| YFK176 | YFK012 x YFK093 | FKR1/fkr1 FKR3/fkr3 | 6 | 24 | 8 | 0 | 0 |
| YFK177 | YFK014 x YFK093 | FKR2/fkr2 FKR3/fkr3 | 0 | 8 | 8 | 0 | 0 |
| YFK030 | YFK001 X YFK005 | FKR X fkr | 0 | 0 | 9 | 0 | 0 |
| YFK036 | YFK003 X YFK009 | FKR X fkr | 0 | 0 | 11 | 0 | 0 |
| YFK213 | YFK045 X YFK007 | FKR1/fkr1 | 0 | 0 | 23 | 0 | 0 |
| YFK228 | YFK005 X YFK023-17A | FKR2/fkr2 | 0 | 0 | 24 | 0 | 0 |

$^a$Diploids created by crossing the parental strains indicated were sporulated, and tetrads were dissected. The FK-506 resistance phenotype of the haploid meiotic progeny were assayed as described in Materials and Methods.
$^b$The relevant genotypes at the fkr1, fkr2, and fkr3 loci are indicated.

TABLE III

The fkr mutants do not exhibit pleitropic drug resistance (pdr) phenotypes

| | | Inhibitory Concentration ($IC_{50}$) (mg/ml) | | | | |
|---|---|---|---|---|---|---|
| Antifungal Antibiotic | Target | YFK005 WT | YFK007 WT | YFK012 fkr1 | YFK014 fkr2 | YFK093 fkr3 |
| Amphotericin B | Membrane Integrity | 1 | 0.8 | 1 | 1 | 1 |
| Anisomycin | Protein Synthesis | 60 | 50 | 60 | 40 | 45 |
| Cycloheximide | Protein Synthesis | 0.03 | 0.03 | 0.03 | 0.02 | 0.02 |
| 5-Fluorocytosine | DNA Synthesis | 0.6 | 0.4 | 1.0 | 0.6 | 0.4 |
| Ketoconazole | Sterol Synthesis | 15 | 15 | 15 | 9 | 8 |
| Lovastatin | Sterol Synthesis | 2 | 3 | 4 | 2 | 4 |
| Monorden | Cell Wall Synthesis? | 5 | 3 | 5 | 3 | 2.5 |
| FK-506 | Unknown | 15 | 22 | >80 | 45 | 50 |
| L-683, 590 | Unknown | 20 | 35 | >80 | 60 | 60 |
| L-683, 742 | Unknown | >80 | >80 | >80 | >80 | >80 |
| Rapamycin | Unknown | 0.06 | 0.06 | 0.06 | 0.04 | 0.03 |

The $IC_{50}$ values were determined by the minimal inhibitory concentration assay described in Materials and Methods.
Data presented are the average of two independent experiments.

TABLE IV

FK-506 resistant mutants (fkr) do not map to FKB1

| | | Ascus Type$^c$ | | |
|---|---|---|---|---|
| Cross$^a$ | Relevant Genotype$^b$ | PD | NPD | T |
| YFK021-5C x YFK164-1D | fkr1/fkb1-1::URA3 | 0 | 2 | 8 |
| YFK023-2B x YFK164-1D | fkr2/fkb1-1::URA3 | 0 | 1 | 5 |
| YFK093 x YFK164-1D | fkr3/fkb1-1::URA3 | 1 | 4 | 2 |

$^a$Diploids created by crossing the parental strains indicated were sporulated, and tetrads were dissected. Uracil auxotrophy was used as a marker to follow the FBK1 locus. The FK-506 resistance phenotype was assayed as described in Materials and Methods.
$^b$The relevant genotypes at the fkr1, fkr2, and fkr3 and fkb1-1 loci are indicated.
$^c$PD, parental ditype; NPD, non-parental ditype; T, tetratype

RESULTS

Three FK-506 analogues exhibit parallel antifungal and immunosuppressive properties. Using antibiotic disc sensitivity assays and the replica plate growth inhibition assay described in the Materials and Methods, we examined the effects of FK-506 on the growth response of several S. cerevisiae strains (25). In these assays, strains YFK005, YFK007 and YFK009 were sensitive to FK-506. Strains YFK001, YFK003 and S288C were found to be resistant to concentrations of FK-506 as high as 100 μg/ml. The resistance phenotype of strains YFK001 and YFK003 were also characterized genetically in crosses with the sensitive strains YFK005 and YFK009, respectively (Table 2). The diploids YFK030 and YFK036 resulting from these crosses were resistant to FK-506 indicating that this phenotype is dominant. Furthermore, the resistance phenotype segregated $2^R:2^S$ in both crosses indicating that it results from single Mendelian genes. The FK-506 sensitive strains YFK005 and YFK007 (Table 1) were chosen for further work, based upon the following criteria. Both strains were sensitive to FK-506 and this phenotype segregated $0^R:4^S$ in crosses (Table 2). The two strains were derived from the diploid YNN216 which is congenic to S288C (37).

A liquid assay was established to quantitate the effects of FK-506 and FK-506 analogues on growth. The three analogues characterized here differ by subtle chemical alterations, as described in the Materials and Methods, which affect their immunosuppressive properties. In in vitro assays measuring T cell activation, FK-506 and the FK-506 analogs L-683,590 and L-683,742 exhibit IC50 values of 0.29, 0.69 and 1.63 nM, respectively (9). FK-506 and the two analogues inhibited vegetative growth of YFK005 in a dose-dependent manner (FIG. 1). FK-506 was the most potent analogue in this assay, exhibiting an $IC_{50}$ value of approximately 10 μg/ml. L-683,742 was the least potent, with an $IC_{50}$ greater than 80 μg/ml. Similar results were observed when the analogues were tested against strain YFK007 (5). Although antibiotic concentrations required to inhibit yeast growth were several orders of magnitude higher than those which block T cell activation, their relative antifungal activities closely paralleled their relative immunosuppressant potencies. These results suggested that molecular recognition of FK-560 in yeast and T cells may be related.

Isolation and characterization of yeast FK-506 resistant (fkr) mutants

To genetically define the molecular element mediating the antifungal activity of FK-506, a process to isolate FK-506 resistant mutants was developed and yeast mutants resistant to inhibitory antibiotic concentrations were isolated. Forty-six spontaneous FK-506 resistant mutants were obtained by plating stationary phase cells (YFK005 and YFK007) on medium containing 40, 80, or 100 μg/ml of FK-506. The mutants arose at a frequency of 1-2 per $10^7$ cells, a frequency expected for single point mutations. Dominance/recessive tests were performed on the mutants by crossing them to a wild-type sensitive strain of opposite mating type, and testing the FK-506 resistance phenotype of the resulting diploids on solid antibiotic-containing medium. In these assays, 23 mutants exhibited dominant phenotypes, 22 mutants possessed co-dominant phenotypes at low antibiotic concentrations, and 1 was recessive. We have named these FK-506 resistant strains, fkr mutants.

Complementation tests were performed on the co-dominant and recessive mutants to begin to determine the number of genes represented. Diploids were isolated by crossing mutants of opposite mating type to one another, and their levels of FK-506 resistance were then tested. The mutations fell into three complementation groups, fkr1, fkr2, and fkr3. The fkr2 mutant YFK014 had the one recessive allele, while 21 fkr1 mutants and the 1 fkr3 mutant (YFK093) exhibited co-dominant phenotypes. Tetrad analyses (described below) confirmed the complementation tests, indicating that at least three complementation groups were defined by single and independent nuclear genes.

Tetrad analyses were performed on crosses between mutants and wild-type strains and between mutants from different complementation groups (Table 2). In crosses between three representative fkr1 mutants (YFK012, YFK045, and YFK054) with wild-type strains, the fkr phenotypes segregated $2^r:2^s$, as expected for mutations in single nuclear genes. Segregation analyses of crosses between these three co-dominant fkr1 mutants confirmed that they contained mutations mapping to a tightly linked locus. Tetrad analysis of a cross between the fkr3 mutant YFK093 and a wild-type strain also indicated that the fkr3 phenotype was conferred by a single mutation (Table 2). Similar analyses of a cross between the fkr2 mutant YFK014 and a wild-type strain indicated that the fkr phenotype of this mutant resulted from two linked mutations, as evidenced by the frequency of parental $(2^r:2^s)$ and tetratype $(3^r:1^s)$ tetrads (Table 2). In tetratype tetrads, these mutations could be distinguished phenotypically by their growth phenotypes at 37° C. (7). The fkr2 mutation conferred a weak temperature-sensitive growth defect at 37° C., while the second fkr mutation exhibited wild-type growth at this temperature. By analyzing the phenotypic patterns of FK-506 resistance and temperature sensitivity in a number of tetratype tetrads derived from diploid YFK023, we identified haploid spores predicted to contain single fkr mutations. One of these spores, YFK023-17A, was shown to contain a single fkr2 mutation (Table 2). In crosses of YFK023-17A (fkr2) with the wild-type strain, the fkr phenotype segregated $2^r:2^s$ in the meiotic haploid progeny. Diploid YFK023 also exhibited a sporulation defect manifested as a prolonged delay in the time required for tetrad development. The fkr2 mutation does not confer the sporulation defect seen in diploid YFK023 (7). YFK023 spores predicted to contain the second fkr mutation present in mutant YFK014 were also crossed to wild-type strains. However, these diploids exhibited a severe sporulation defect, preventing the tetrad analysis necessary to confirm the genetic nature of this allele.

Crosses between mutants from different complementation groups indicated that the fkr1, fkr2, and fkr3 mutations map to independent loci (Table 2). Parental tetrads $(r^r:0^s)$ would be expected meiotic progeny from these crosses if fkr complementation groups mapped to the same or tightly linked loci. Tetratype tetrads $(3^r:1^s)$ were the predominant segregation pattern observed in crosses between representative fkr1 and fkr3 mutants, indicating that these loci are not linked. Parental $(4^r:0^s)$ and nonparental ditype $(2^r:2^s)$ tetrads were also observed at the expected frequencies. Tetratype tetrads were also the predominant pattern of segregation observed in a cross between two representative fkr1 mutants and the fkr2 mutant YFK023-2B, indicating that fkr1 and fkr2 are not linked. YFK023-2B contained both tightly linked fkr mutations present in YFK014 (7). In the cross between the fkr2 and fkr3 mutants, tetratype $(3^r:1^s)$ and nonparental ditype $(2^r:2^s)$ tetrads were recovered at approximately equal frequencies, indicating that these mutations define two independent complementation groups.

Figure 2A:
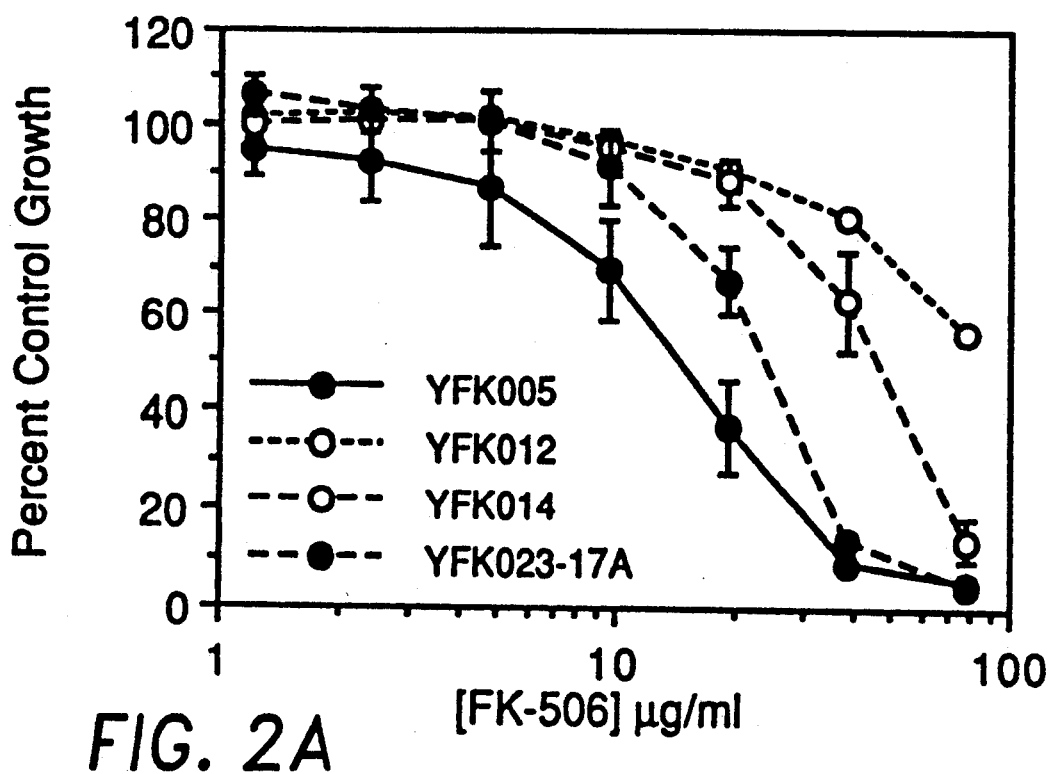
FIG. 2 illustrates that the fkr mutants exhibit varying degrees of FK-506 resistance. The levels of FK-506 resistance of the fkr1 (YFK012), fkr2 (YFK014 and YFK023-17A) and fkr3 (YFK093) mutants were examined in liquid culture, and compared with their wild-type parental strains, YFK005 and YFK007, and results are presented as the percent of control growth in the absence of antibiotic.
Figure 2B:
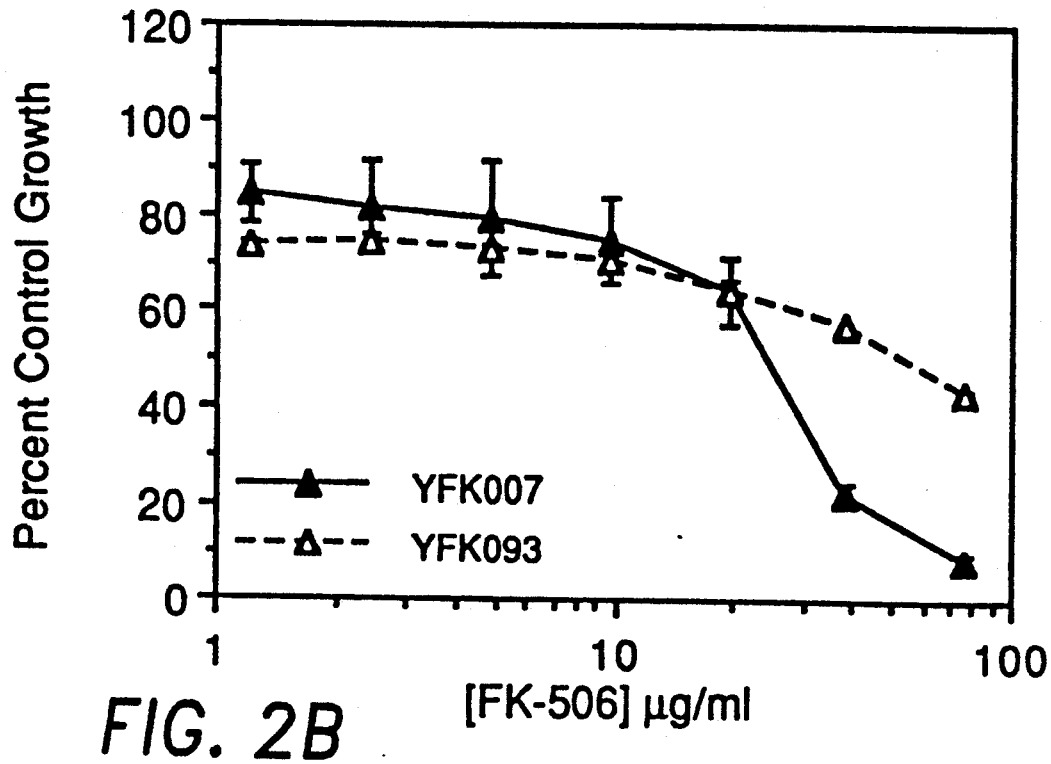

These mutants were also distinguishable by their levels of FK-506 resistance. Strains YFK012, YFK045, and YFK054 are fkr1 mutants which were isolated at different concentrations of FK-506 and found to be resistant to antibiotic concentrations as high as 80 to 100 μg/ml. The level of KF-506 resistance of YFK012 is illustrated in FIG. 2A. The original mutant YFK014, harboring fkr2 and a second tightly linked fkr mutation, was isolated at an antibiotic concentration of 40 μg/ml; however, the mutant was sensitive to FK-506 at concentrations of 80 to 100 μg/ml (FIG. 2A). The level of resistance of the fkr2 mutant YFK023-17A is slightly lower than that of YFK014 (FIG. 2A), indicating that both fkr mutations in YFK014 contribute to the level of resistance of this mutant. This was evident in replica plate and spot test assays of YFK014, YFK023-17A, and mutants containing the second tightly linked fkr locus (7). Mutant YFK093 (fkr3) was isolated at an antibiotic concentration of 80 μg/ml and had a level of resistance intermediate to that of the fkr1 and fkr2 strains (FIG. 2B).

In yeast, several pleiotropic drug resistance (pdr) mutations confer cross-resistance to multiple antibiotics of unrelated structure and mode of action (1,10,22,27,40). Most of these mutations also confer resistance to the protein synthesis inhibitor cycloheximide. To determine whether the fkr phenotypes are typical of known pdr mutations, we examined the mutants' resistance to a panel of antifungal antibiotics by conventional MIC assays (16). The test antibiotics chosen were structurally and functionally unrelated, and included amphotericin B, anisomycin, cycloheximide, 5-fluorocytosine, ketoconazole, lovastatin, and monorden (Table III). The rapamycin sensitivity of each mutant was also examined because of the antibiotic's relatedness to FK-506. None of the mutants exhibited dramatic increases in their levels of resistance to any of the antibiotics tested. Two fkr1 mutants exhibited an approximate 5-fold increase in their levels of resistance to FK-506 and L683,590, but only a marginal 1.5 to 2-fold increase in lovastatin and 5-fluorocytosine resistance. The fkr3 mutant exhibited a 2.5 to 3-fold increase in its level of FK-506 resistance, and no dramatic change in resistance to the other antibiotics, except ketoconazole to which it was 2-fold more sensitive. The fkr2 mutant exhibited a minor, but reproducible increase in sensitivity to several antibiotics, including anisomycin, cycloheximide, ketoconazole and monorden. These results suggest that the mutants' fkr phenotypes did not result from typical pdr mutations. We have also published results indicating that two pleiotropic drug resistance mutations (pdr1) do not confer the KF506 resistance phenotype associated with the fkr mutations (52).

The FKR and FKB1 LOCI ARE DISTINCT

Figure 3A:
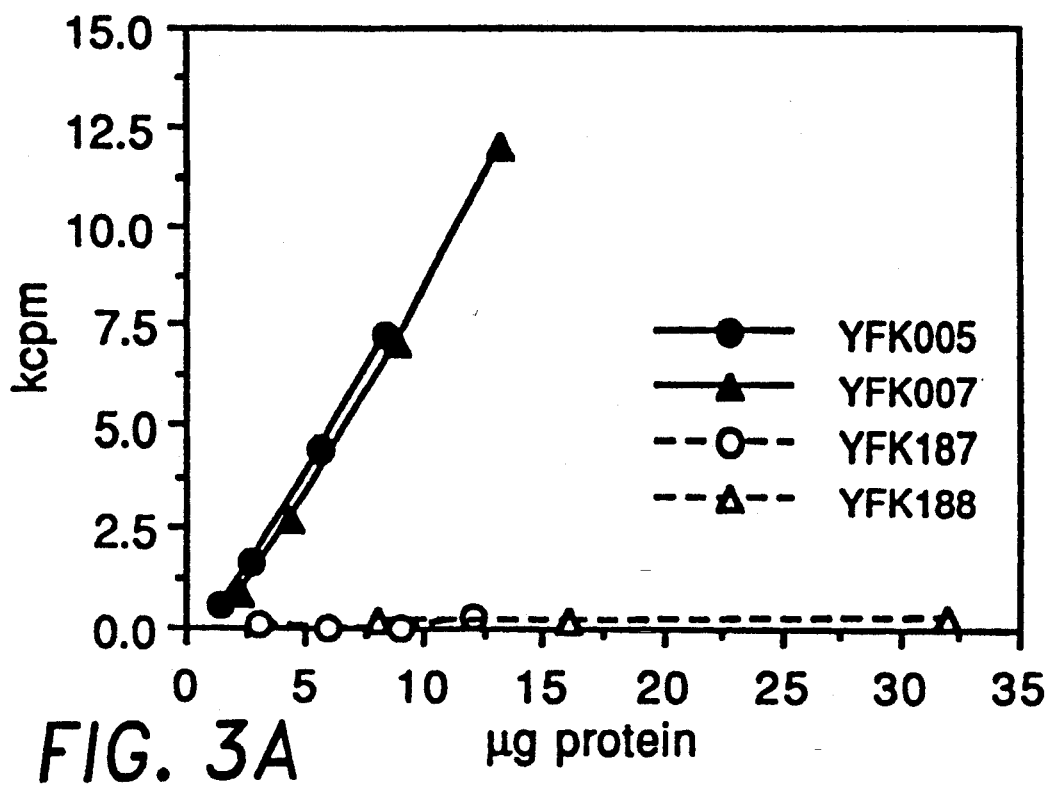
FIG. 3 illustrates that FK-506 binding activity is not affected by the fkr mutations. (A) Levels of FK-506 binding activity present in fkb1-Δ2 null mutants (YFK187 and YFK188) and their wild type strains (YFK005 and YFK007) were assayed using [$^3$H]dihydro-FK-506. (B) FK-506 binding activity of the fkr strains YFK012 (fkr1), YFK014 (fkr2), YFK093 (fkr3) and the wild type parental strains YFK005 and YFK007.
Figure 3B:
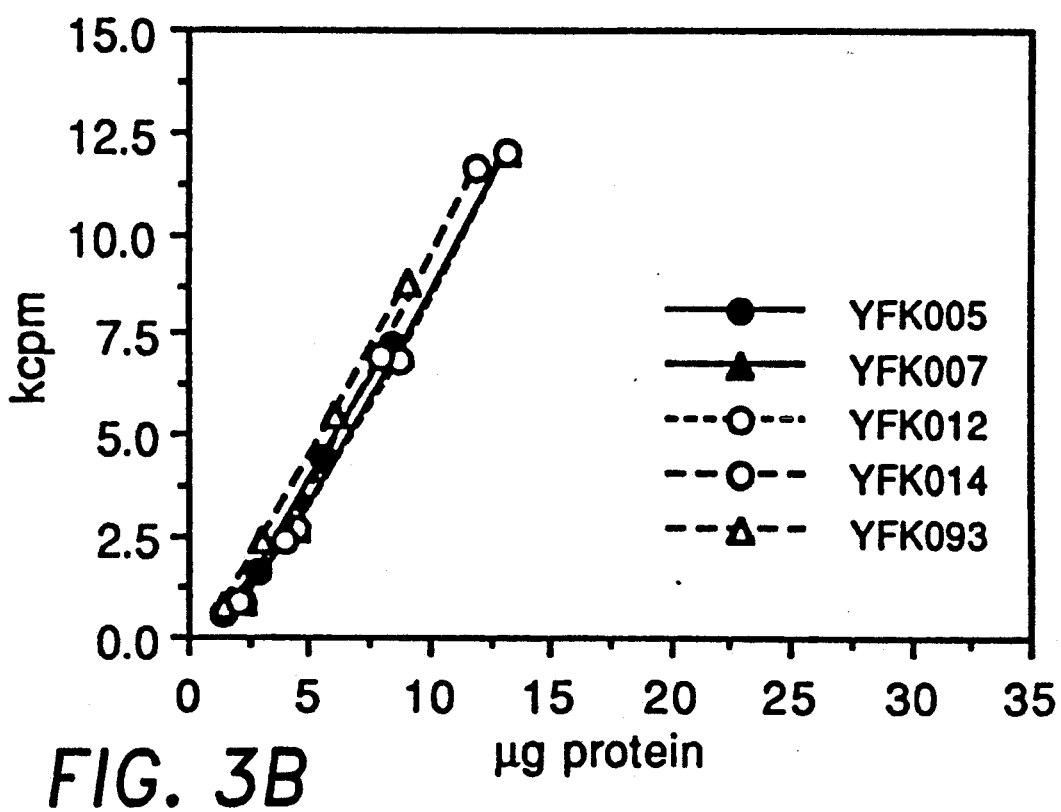

FKBP is an abundant cytosolic FK-506 binding protein first discovered in calf thymus, human spleen and the Jurkat T cell line (15,33,34). This ubiquitous and highly conserved receptor has been found in a variety of mammalian tissues, as well as simple eukaryotes (35,48). Like mammalian FKBPs, the yeast binding protein binds FK-506 and shares equivalent masses and immunological crossreactivity with antibodies generated against bovine FKBP (35). FKBP's phylogenetic conservation is clearly reflected by the 57% amino acid identity shared by yeast and human FKBP (50). To determine if the fkr mutations dramatically affected the ligand-binding of yeast FKBP, we assayed the levels of FK-506 binding activity in the mutants, and compared them with the levels found in wild-type and fkb1-Δ2 strains. The yeast FKB1 gene encodes the major yeast FKBP and strains carrying fkb1 null alleles contained less than 1% the level of FK-506 binding activity assayed in wild-type cells (FIG. 3A; 50). However, each of the fkr mutants possessed wild-type levels of FKBP (FIG. 3B).

Figure 4A:
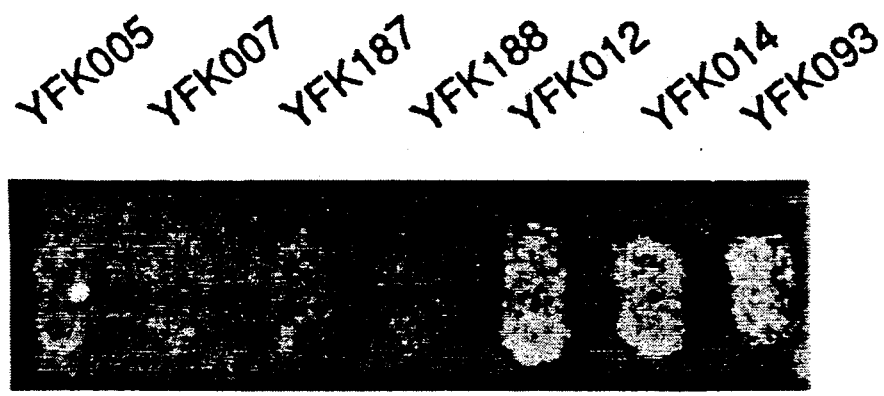
FIG. 4 illustrates that fkb1 null mutations do not confer an fkr phenotype. (A) Replica plate assay for FK-506 sensitivity of wild-type strains (YFK005 and YFK007), strains carrying the fkb1-Δ2 null allele (YFK187 and YFK188), and the fkr mutants, YFK012 (fkr1), YFK014 (fkr2), YFK093 (fkr3). (B) FK-506 sensitivity of the fkb1-Δ2 null mutants (YFK187 and YFK188) and their wild-type parental strains (YFK005 and YFK007) assayed in liquid culture. Results are presented as the percent of control growth in the absence of any antibiotic.
Figure 4B:
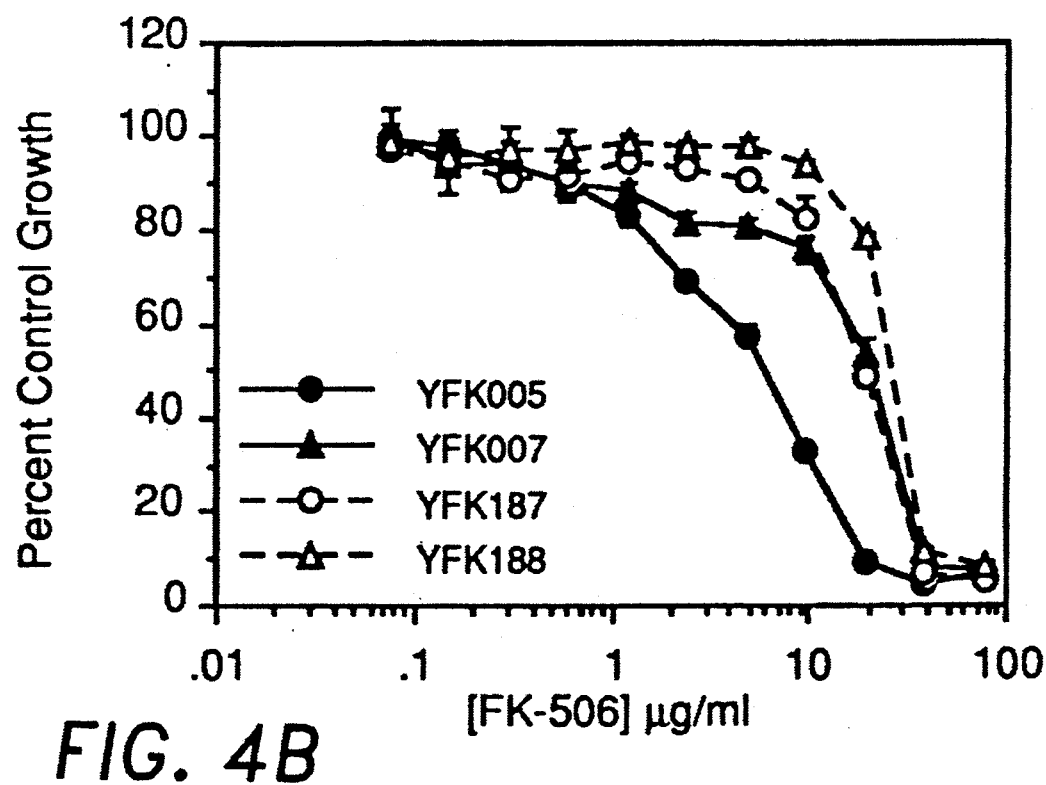

The resistance phenotype of fkb1 null mutants was also assessed. The effects of FK-506 on the growth of two fkb1-Δ2 mutants on solid medium (YFK187 and YFK188) were compared to their wild-type parental strains (YFK005 and YFK007) and to fkr1, fkr2, and fkr3 mutants (YFK012, YFK014 and YFK093), respectively (FIG. 4A). Both fkb1-Δ2 mutants and their parental strains were unable to grow on solid antibiotic-containing medium permissive for the fkr mutants. When growth was assayed in liquid medium, the fkb1-Δ2 mutants exhibited a marginal, but reproducible increase in resistance over their wild-type parental strains (FIG. 4B). However, this small increase did not confer a selectable fkr phenotype on solid medium in our assays, as shown above. Similar results were seen with fkb1-Δ1 mutants (4), suggesting that depletion of FKBP from yeast cells is not sufficient to confer a dramatic fkr phenotype to vegetative cells.

Finally, to determine whether any fkr mutants contained fkb1 mutations that did not have a null phenotype, but were otherwise impaired, we crossed fkr and fkb1::URA3 strains, and analyzed the segregation patterns of fkr resistance and uracil auxotrophyos solid medium (Table 3). The frequencies of non-parental ditype and tetratype tetrads in these crosses demonstrated that the fkr mutations do not map to FKB1.

FKB1-Δ NULL MUTATIONS CONFER A DRAMATIC INCREASE IN RAPAMYCIN RESISTANCE

Figure 5:
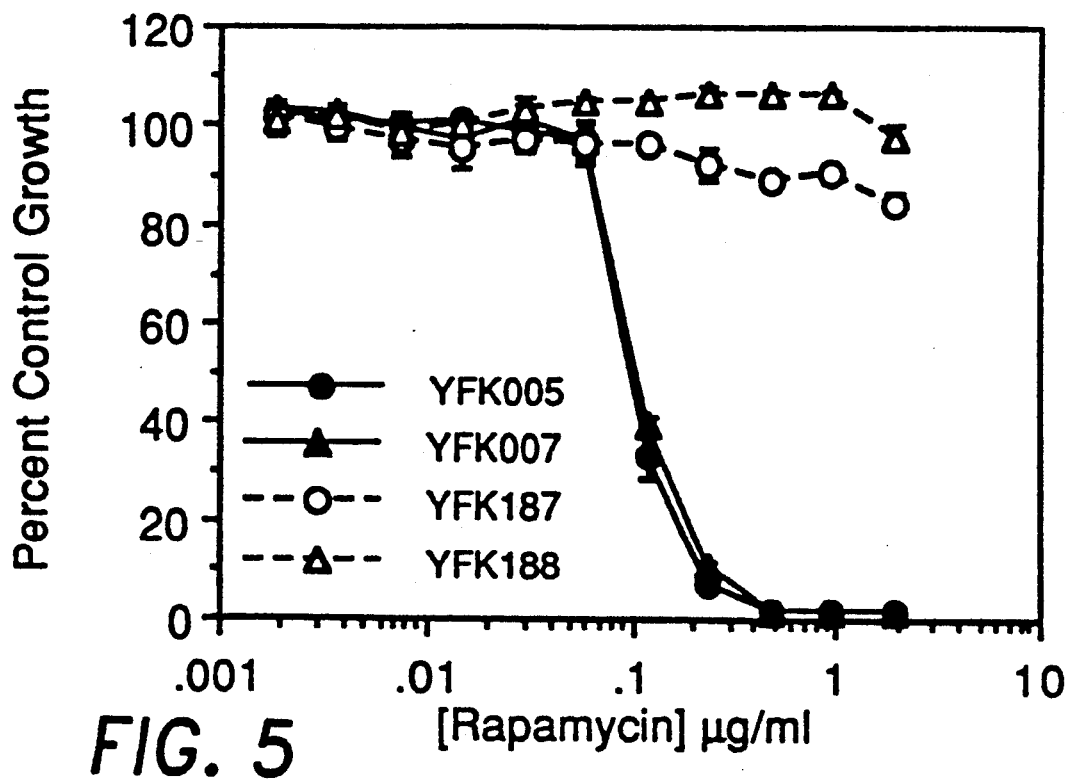
FIG. 5 illustrates that FKBP mediates rapamycin sensitivity in yeast. The rapamycin sensitivity of strains carrying the fkb1-Δ2 null allele (YFK187 and YFK188) were compared to that of their wild-type parental strains (YFK005 and YFK007) in liquid culture, and results are presented as the percent of control growth in the absence of any antibiotic.

FK-506 and rapamycin antagonize each others immunosuppressive activities (2,8) and bind to human FKBP with similar affinities (2). To determine whether the antifungal properties of rapamycin were mediated by yFKBP, we examined the ability of yFKBP to bind rapamycin and compared the activity of rapamycin against fkb1-Δ2 mutants and wild-type strains. The macrolide antibiotic potently inhibited vegetative growth of the wild-type strains YFK005 and YFK007 (FIG. 5), exhibiting an $IC_{50}$ value of 0.1 $\mu$g/ml which is significantly lower than the $IC_{50}$ for FK-506 (10 $\mu$g/ml) in the same assay. In striking contrast to their response to FK-506, the fkb1-Δ2 mutants YFK187 and YFK188 exhibited a dramatic rapamycin resistance, growing in the presence of 10–20 fold higher concentrations of antibiotic. These results indicate that yFKBP plays a major role in mediating the growth inhibitory properties of this antibiotic.

THE PRODUCT OF THE FKR3 GENE RESPONDS TO FK-506

Figure 6:
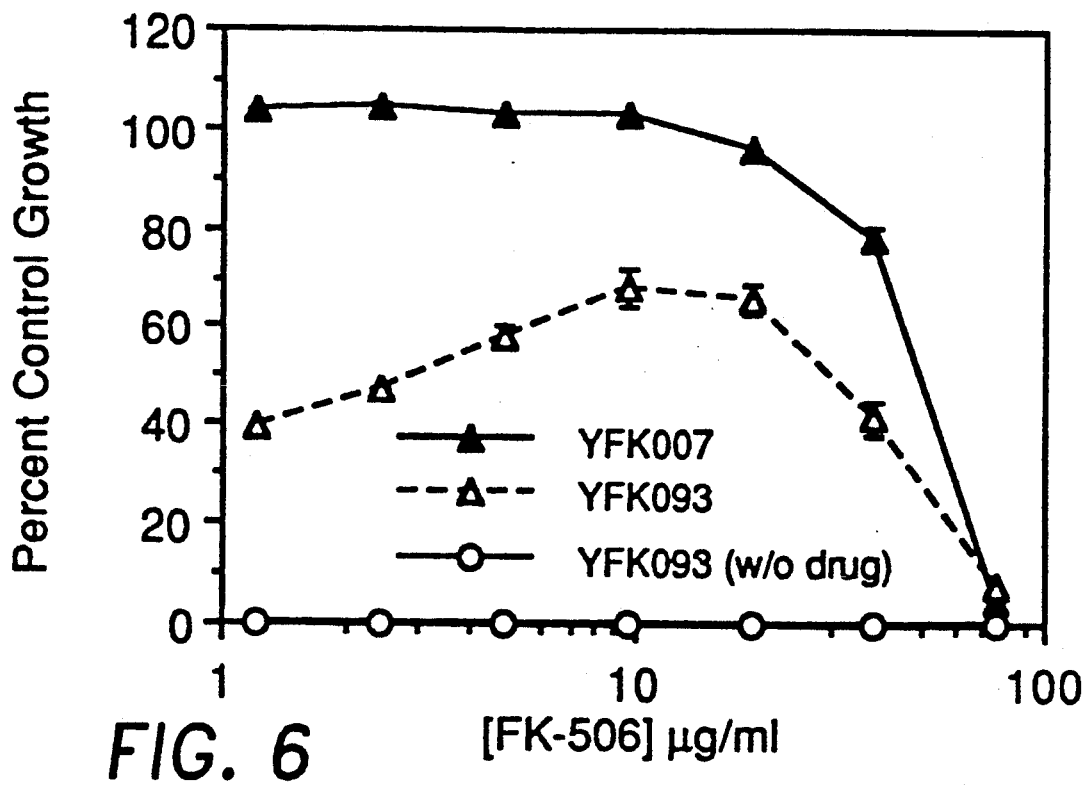
FIG. 6 illustrates that the temperature sensitive growth defect of the fkr3 mutant is suppressed by FK-506. The growth response of the fkr3 mutant (YFK093) and its wild-type parental strain (YFK007) at 37° C. were assayed in liquid culture in the presence of FK-506 after 41 hours. Results are presented as the percent of control growth of the wild-type strain in the absence of any antibiotic.

We further examined the fkr mutants for additional phenotypes, in an attempt to clarify the cellular pathways which are responsive to FK-506. We discovered that the fkr3 mutant, YFK093, exhibited a recessive temperature sensitive growth defect reversible by FK-506. This mutant was isolated at 30° C., but was unable to grow at 37° C., suggesting that the FKR3 product is essential for vegetative growth. The cosegregation of the fkr and ts phenotypes in 25 four-spore tetrads derived from an FKR3/fkr3 heterozygote (5) suggests that these phenotypes result from a single fkr3 mutation. The most interesting fkr3 phenotype was the mutant's response to FK-506 at the non-permissive temperature. FK-506 partially suppressed the mutant's ts phenotype in a dose-dependent fashion (FIG. 6). After prolonged growth at 37° C. in the presence of low concentrations of FK-506 (1–20 $\mu$g/ml), the mutant achieved 35–70% of the stationary level of growth of its wild-type parent. At higher antibiotic concentrations, growth of the mutant was inhibited. Similar results were observed with the FK-506 analogue L-683,590 (5). These conditional fkr3 phenotypes suggest that the product of this gene interacts with or responds to FK-506.

DISCUSSION

FK-506, rapamycin and CsA are powerful pharmacologic probes for studying the complex process of T cell activation. The antifungal properties of these antibiotics and the phylogenetic conservation of their immunophilin receptors suggest that fungi might provide powerful genetic systems for studying the antibiotics' diverse biological activities. Our observation that three FK-506 analogues exhibit parallel antifungal and immunosuppressive potencies further suggests that yeast may provide a useful system for studying FK-506. A concern, however, is the antibiotic's low potency against yeast. This may simply result from permeability problems presented by the cell wall or plasma membrane. However, the potency of the structurally related macrolide rapamycin at nM concentrations, as well as the measurable response of the fkr3 mutant to FK-506 concentrations as low as 1 μg/ml at 37° C., suggest that permeability problems are not sufficient to explain the antibiotic's poor anti-yeast activity. Alternatively, this poor potency may be related to the nature of our assay, which measures growth inhibition of undifferentiated cells. FK-506 specifically inhibits T cell activation at nM concentrations (for review see 36,43). Once activated, through, lymphocyte proliferation is resistant to the antibiotic, suggesting that FK-506 affects an early activation step associated with exit from $G_o$ (24). We have observed that exponentially growing cells are indeed more resistant to FK-506 than stationary cells (4), suggesting that FK-506 is also less potent as an inhibitor of yeast cell proliferation. Rapamycin is a potent inhibitor of lymphokine-dependent T cell proliferation and appears to block a later step in the T cell activation process, consistent with this reasoning.

We isolated yeast FK-506 resistant (fkr) mutants to identify proteins which interact with or respond to the antibiotic in vivo. The genetic and physiological properties of the co-dominant and recessive mutants described in this paper indicate that our selection process uncovered mutations in at least three genes. In addition, the dominant mutations obtained, but not yet fully characterized, may represent new alleles of the fkr loci described or may identify additional fkr genes.

Several phenotypes of the isolated mutants provide insights into the nature of their mutations. First, the fkr mutants do not exhibit typical pleiotropic drug resistance traits, suggesting their phenotypes do not result from non-specific pdr alterations. Secondly, none of the fkr mutations affect the levels of yFKBP measured in vitro. These results differ from the findings that *S. cerevisiae* and *N. crassa* CsA resistance mutations dramatically reduce the levels of cyclophilin which is competent to bind CsA (47). Our genetic analyses of the fkr loci confirm that they do not map to FKB1, eliminating the formal possibility that they encode fkb1 mutations which alter yFKBP's responsiveness to FK-506 without significantly affecting receptor ligand-binding properties. The response of yeast fkb1 null mutants to FK-506 and rapamycin are also informative. The fkb1 null mutations abolish detectable yFKBP activity measured in vitro, confer a dramatic rapamycin resistance to cells, and have marginal effects on their response to FK-506. To explain these phenotypes, we suggest that yFKBP mediates the antifungal activity of rapamycin and that another FK-506 binding protein(s) is the major mediator of FK-506 cytotoxicity. This protein must constitute a small fraction of the total FK-506 binding activity in vegetative cells. Yeast FKBP might also mediate more sensitive FK-506 responses in other cellular processes.

The product of the FKR3 gene is an attractive candidate for a protein which interacts with or responds to FK-506. The fkr3 mutant's diverse phenotypes have several important implications. Its response to low FK-506 concentrations is the most sensitive phenotype we have detected, and begins to approach the antibiotic concentration required to block T cell activation. The biphasic nature of this response also suggests that FK-506 interacts with multiple targets, or that antibiotic interactions with a single target have pleiotropic effects depending on the antibiotic concentration within the cell. More importantly, FKR3 is an FK-506 responsive gene or gene product which is distinct from FKB1.

Several models to explain the pleiotropic responses of the fkr3 mutant to FK-506 and its recessive ts phenotype are plausible. An implicit assumption of each model is that the fkr3 mutation is a subtle structural change in a gene or gene product which responds to FK-506. Moreover, this mutation has dramatic phenotypic consequences on cells grown in the presence and absence of FK-506. The following model is attractive. We propose that FK-506 inhibits growth of wild-type cells by interacting with and antagonizing the function of one or more cellular proteins, one of which is FKR3. At permissive temperatures, the mutant protein is able to bind, but not respond to FK-506 efficiently. Elevated temperatures alter FKR3 conformation such that the protein's function and cell growth are inhibited. When the mutant is grown at 37° C. in the presence of low concentrations of FK-506, the antibiotic transiently binds to the protein, stabilizing it. This transient binding of FK-506 stabilizes FKR3 sufficiently to enable it to function, thereby suppressing the mutant's conditional growth defect. At higher antibiotic concentrations, however, the binding sites of the protein are saturated, and FKR3 activity, and subsequently cell growth, are inhibited. This overall hypothesis is currently being addressed by a detailed molecular and biochemical analysis of FKR3 and its product.

The results described in this disclosure clearly indicate that FKR3 responds to FK-506. Questions of whether FKR3 interacts with yFKBP or lies in a common drug-responsive pathway will be testable by examining the phenotypes of fkr3 fkb1 double mutants. Several lines of evidence suggest that FK-506 and rapamycin interact with FKBP to inhibit distinct signal transduction pathways important for T lymphocyte activation (2,7,8). Do common or distinct antibiotic responsive pathways exist in yeast? Our observation that depletion of yeast FKBP confers resistance to rapamycin and non to FK-506, and that the fkr mutants exhibit wild-type sensitivity to rapamycin, suggest this is the case. Moreover, they demonstrate that yeast will provide a powerful model to refine these biological issues.

EXAMPLES

Materials and Methods

Yeast strains and genetic methods

Standard procedures for mating, diploid isolation, complementation testing, sporulation, and tetrad analysis were used (30). All *S. cerevisiae* strains used in this study are listed in Table 1. Strains YFK005 and YFK007 are congenic to S288C and are available from John Hopkins University, (identified as YPH54 and YPH98, respectively; 37). Both are FK-506 sensitive. YFK012 (fkr1), YFK014 (fkr2), YFK045 (fkr1), and YFK054 (fkr1) are spontaneous FK-506 resistant mutants isolated from YFK005. YFK093 (fkr3) is a spontaneous FK-506 resistant mutant isolated from YFK007.

These mutants were isolated as pure strains as described below. YFK021-5C and YFK059-8B are haploid strains generated by crossing YFK007 with YFK012 or YFK054, respectively. YFK023-2B, YFK023-3B, and YFK023-17A are haploid meiotic progeny from a cross of strains YFK007 and YFK014. YFK164-1D (fkb1-delta-1) is a haploid strain derived from diploid strain YFK164 (FKB1/fkb1-delta-1) (50). TFK164 was constructed by introducing a single fkb1-delta-1 null allele into diploid YFK016 (Table 2) by one-step gene replacement (26). The fkb1-$\Delta$2 mutants YFK187 and YFK188 were derived from YFK005 and YFK007, respectively, by one-step gene replacement (26) with the fkb1-$\Delta$2 null allele described below. The $\alpha$-factor super-sensitive strain DJ211.5.3 was used in halo assays (38) to determine the mating type of haploid spores derived by tetrad dissection.

Media

YPAD, SC, amino acid drop-out, and SPO media have been described (30). Solid SC medium containing FK-506 was prepared by addition of antibiotic to 40 ml of autoclaved SC medium cooled to 52° C. The antibiotic-containing medium was then dispensed to petri dishes in 20 ml aliquots. Liquid SC medium was filtered sterilized.

YPAD

A complex medium used for the preparation of slants. The adenine is added to inhibit the reversion of ade 1 and ade 2 mutants.

| | |
|---|---|
| 1% Bacto-yeast extract | 10 g |
| 2% Bacto-peptone | 20 g |
| 2% Dextrose | 20 g |
| 0.006% Adenine sulfate | 60 mg |
| Distilled water | 1000 ml |
| 2% Bacto-agar | 20 g |

The medium is dissolved in a boiling water bath and 1.5 ml portions are dispensed with an automatic pipetter into 1 dram vials. The caps are screwed on loosely, and the vials are autoclaved. After autoclaving, the rack is inclined so that the agar is just below the neck of the vial. The caps are tightened after one or two days.

SD

A synthetic minimal medium containing salts, trace elements vitamins, nitrogen source (Bacto-yeast nitrogen base without amino acids) and dextrose.

| | |
|---|---|
| 0.67% Bacto-yeast nitrogen base without amino acids | 6.7 g |
| 2% Dextrose | 20 g |
| 2% Bacto-agar | 20 g |
| Distilled water | 1000 ml |

Synthetic Complete Medium (SC)

The synthetic minimal medium with various constituents is prepared by adding the following complete amino acid mix to SD medium (above):

| | Complete Amino Acid Mix | | | |
|---|---|---|---|---|
| | 0.8 g | 4 g | Adenine | Sigma A9126 |
| | 0.8 | 4 | L-Arginine | Sigma A5131 |
| A | 4.0 | 20 | L-Aspartic Acid | Sigma A9256 |
| | 0.8 | 4 | L-Histidine | Sigma H8125 |
| | 1.2 | 6 | L-Isoleucine | Sigma I2752 |
| | 2.4 | 12 | L-Leucine (2X CSH) | Sigma L8000 |
| | 1.2 | 6 | L-Lysine | Sigma L5626 |
| | 0.8 | 4 | L-Methionine | Sigma M9625 |
| | 2.0 | 10 | L-Phenylalanine | Sigma P2126 |
| A | 8.0 | 40 | L-Threonine | Sigma T8625 |
| | 0.8 | 4 | L-Tryptophan | Sigma T0254 |
| | 1.2 | 6 | L-Tyrosine | Sigma T3754 |
| | 0.8 | 4 | Uracil | Sigma U0750 |
| | 6.0 | 30 | L-Valine | Sigma V0500 |
| | 30.8 g | 154 g | | |
| | 35.4 | 144 | 1L aliquots | |
| | N1200 | N6000 | petris | |

A - n.b. L-Aspartic Acid and L-Threonine breakdown upon autoclaving.

| SC Medium | | | |
|---|---|---|---|
| 0.870 g | 0.522 g | 1.566 g | Complete Amino Acid Mix |
| 6.7 | 4.02 | 12.06 | Bacto-yeast nitrogen base w/out amino acids |
| 20 | 12 | 36 | Dextrose |
| 1000 ml | 600 ml | 1800 ml | dWater to volume |
| 20 | 12 | 3 × 12 | Bacto-Agar |

ANTIFUNGAL ANTIBIOTICS

The chemical structures of FK-506 and rapamycin have been reported (11,42). FK-506, L-683,590 identical to FR-900520, of Fujisawa), L-683,742, the C-31 desmethyl analog of FR-900520, disclosed in EP O 349,061, lovastatin (U.S. Pat. No. 4,231,938 to Merck & Co. Inc.) monorden, disclosed in Nature, Vol. 171, p. 344 (1953), and rapamycin (U.S. Pat. No. 3,919,992). L-683,590 (FR 900520) is an FK-506 analog containing an ethyl substituent replacing the allyl moiety at position C21 of the macrolide ring. L-683,742 contains this substitution, as well as a hydroxyl moiety in place of the 0-methyl substituent at position C31. Amphotericin B, anisomycin, cycloheximide, 5-fluorocytosine, and ketoconazole were purchased from Sigma Chemical Co. (St. Louis, Mo.). Stock solutions of the antibiotics were prepared in methanol.

MICROTITER GROWTH INHIBITION ASSAY

The antifungal activity of each of the above antibiotics and/or immunosuppressant was determined by conventional MIC assays (16). Starter cultures of strains were grown to stationary phase in SC medium at 28° C. for 48 hrs. Cell densities were measured optically at 660 nm ($OD_{660}$). Assays were performed in flat-bottom 96 well microtiter plates. Serial dilutions of antibiotic-containing SC medium were performed in microtiter plates so that each well contained a two-fold lower concentration of antibiotic than the previous well. After serial dilutions, each well contained 50 $\mu$l of SC medium with antibiotic. 0.2 ml of inoculated culture ($2 \times 10^5$ cells/ml) was added to each well, and incubated at 28° or 37° C. for 24–45 hrs. Cell growth was measured optically at 620 nm ($OD_{620}$) on a microtiter plate reader (SLT Lab Instruments SLT340 ATTC). The percent control growth for strains which exhibited a temperature sensitive phenotype at 37° C. was expressed at the percent of wild-type growth in the absence of antibiotic. The value reported represent the average ($\pm$SD) of two or more independent samples.

REPLICA PLATE AND SPOT TEST GROWTH INHIBITION ASSAYS

A replica plate assay to detect FK-506 sensitivity was developed, and used to score the resistance phenotypes of various strains. Strains were patched onto solid YPAD medium lacking antibiotic, incubated at 28° C. for two days, and then replica plated onto solid SC medium containing either 40, 80, or 100 μg/ml of FK-506, followed by growth at 28° C. for two days. Cells were then replica plated onto a second SC plate containing the same concentration of drug and their growth was scored after two days.

An alternative spot test assay used to score the resistance phenotypes of strains was performed as follows. Strains were inoculated into 150 μl of SC medium in microtiter dishes and grown to stationary phase at 28° C. for 2 days. 4 μl of cells were spotted onto solid SC medium containing 40 or 80 μg/ml FK-506 and incubated at 28° C. for 4 days. Growth was scored (measured) each day.

ISOLATION OF MUTANTS RESISTANT TO FK-506

Spontaneous FK-506 resistant mutants were selected from strains YFK005 and YFK007 by plating cells onto medium containing inhibitory concentrations of FK-506. Cells were grown to stationary phase in SC medium at 30° C. for two days, to allow the generation of spontaneous mutants, and then plated onto the same medium containing 40, 80, or 100 μg/ml of FK-506, at a concentration of $1 \times 10^7$ cells/plate. Colonies which arose on antibiotic-containing media after two to three days at 30° C. were clonally purified on SC medium containing antibiotic at the same concentration at which they were isolated. Because each mutant was not isolated independently, the selection procedure was performed twice to ensure isolation of independent mutants.

To identify mutants exhibiting the temperature sensitive phenotypes, i.e. YFK 093, colonies were patched onto solid YPAD medium, incubated at 28°–30° C. and replica plated to YPAD which was incubated at 37° C. Growth was evaluated after 2 days. The 37° C. plate was then replica plated to a second YPAD plate and incubated at 37° C. to confirm the original observation. The FK-506 dependence of strain YFK 093 at 37° C. was determined in the FK-506 microtiter assay described, supra, using FK-506 as the antibiotic.

fkb1 null alleles

The fkb1-Δ1 disruption allele of FKB1 has been described (50). It contains the URA3 gene inserted at amino acid position 30 of the 114 amino acid yFKBP, oriented so that transcription of URA3 is opposite that of FKB1. The fkb1-Δ2 allele was constructed by deleting an NruI fragment from the plasmid containing fkb1-Δ1, resulting in a disrupted FKB1 allele deleted of all coding sequences 3' to the insertion.

FK-506 binding assays on yeast extracts

Total cellular protein extracts were prepared from 6 ml of stationary phase cells by glass bead-breakage in 0.3 ml of buffer (150 nM Tris (pH 7.5), 10 nM MgCl$_2$, 1 nM dithiothreitol, 10% (vol/vol) glycerol, 1 nM phenylmethylsulfonyl fluoride, benzamidine at 3 μg/ml, aprotinin at 1 μg/ml, and leupeptin at 1 μg/ml) as described previously (50). After removal of insoluble material by centrifugation for 15 min. in a microcentrifuge, the extracts were assayed using a standard [$^3$H]-FK-506 binding assay (34). Briefly, 0.15 μCi of [$^3$H]-dihydro-FK-506 (45–50 mCi/mg) was incubated with protein extract in 20 nM sodium phosphate (pH 7.2), 0.5% BSA for 15–20 minutes at room temperature. Protein bound [$^3$H]-FK-506 was separated from free radioligand by chromatography on Sephadex LH-20 columns (Pharmacia) as described. Free [$^3$H]-dihydro-FK-506 is retained on the lipophilic LH20 resin while protein bound ligand flows through the column. Flow through fractions containing protein bound [$^3$H]-FK-506 were mixed with 3.0 ml of Aquasol-2 and counted in a scintillation counter. Protein concentrations were determined by the Bradford assay (3) using BSA as a standard.

REFERENCES

1. Balzi, E., Chen, W., Ulaszewski, S., Capieaux, E., and Goffeau, A. 1987. The multidrug resistance gene PDR1 from *Saccharomyces cerevisiae*. *J. Biol. Chem.* 262: 16871–16879.

2. Bierer, B. E., Mattila, P. S., Standaert, R. F., Herzenberg, L. A., Burakoff, S. J., Crabtree, G., and Schreiber, S. L. 1990. Two distinct signal transmission pathways in T lymphocytes are inhibited by complexes between an immunophilin and either FK506 or rapamycin. *Proc. Natl. Acad. Sci. USA* 87; 9231–9235.

3. Bradford, M. 1976. A rapid and sensitive method for the quantification of protein utilizing the principle of protein-dye binding. *Anal. Bioch.* 72: 248–254.

4. Brizuela, L. (1991). Unpublished data.

5. Chrebet, G. and Parent, S. A. (1991). Unpublished data.

6. Dreyfuss, M., Harri, E., Hofmann, H., Kobel, H., Pache, W., and Tscherter, H. 1976. Cyclosporin A and C. *Eur. J. Appl. Microbiol.* 3: 125–133.

7. Dumont, F. J., Staruch, M. J., Koprak, S. I., Melino, M. R. and Sigal, N. H. 1900. Distinct mechanisms of suppression of Murine T cell activation by the related macrolides FK506 and Rapamycin. *J. Immunol.* 144: 251–258.

8. Dumont, F. J., Melino, M. R., Staruch, M. J., Koprak, S. I., Fischer, P. A., and Sigal, N. H. 1990. The immunosuppressive macrolides FK506 and Rapamycin act as reciprocal antagonists in Murine T cells. *J. Immunol.* 144: 1418–1424.

9. Dumont, F. J. (Merck Sharp and Dohme Research Laboratories). (1991). Personal Communication.

10. Falco, S. C., Dumas, K. S., McDevitt, R. E., and Golin, J. E. 1986. Molecular biology of sulfonylurea herbicide action on *Saccharomyces cerevisiae*, p. 99–104 In Stewart, G. G., Russell, L., Kelin, R. D., and Hiebsch, R. R. (eds) Biological Research on Industrial Yeasts, vol III. CRC Press, Boca Raton, Fla.

11. Findlay, J. and Radics, L. 1980. On the chemistry and high field nuclear magnetic resonance spectroscopy of rapamycin. *Can. J. Chem.* 58, 579–590.

12. Fisher, G., Wittman-Liebold, B., Lang, K., Kiefhaber, T. and Schmid, F. X. 1989. Cyclophilin and peptidyl-prolyl cis-trans isomerase are probably identical protein. *Nature* 337: 476–478.

13. Haendler, B., Keller, R., Hiestand, P. C., Kocher, H. P., Wegmann, G., and Rao Movva, N. (1989). Yeast cyclophilin: isolation and characterization of the protein, cDNA and gene. *Gene* 83: 39–46.

14. Handschumacher, R. E., Harding, M. W., Rice, J., Drugge, R. J., and Speicher, D. W. 1984. Cyclophilin: a specific cytosolic binding protein for cyclosporin A. *Science* 226: 544–547.

15. Harding, M. W., Galat, A., Uehling, D. E. and Schreiber, S. L. 1989. A receptor for the immunosuppressant FK-506 is a cis-trans peptidyl-prolyl isomerase. *Nature* 341: 758–760.

16. Harwick, H. J., Weiss, P. and Fekety, F. R. 1968. Application of microtitration techniques to bacteriostatic and bactericidal antibiotic susceptibility testing. *J. Lab. Clin. Med.* 72: 511–516.

17. Kino, T., Hatanaka, H., Hashimoto, M., Nishiyama, M., Goto, T., Okuhara, M., Kohsaka, M., Aoki, H., and Imanaka, H. 1987. FK506, a novel immunosuppressant isolated from Streptomyces. I Fermentation, isolation, and physico-chemical and biological characteristics. *J. Antibiotics* 40: 1249–1255.

18. Kino, T., Hatanaka, H., Miyata, S., Inamura, N., Nishiyama, M., Yajima, T., Goto, T., Okuhara, M., Kohsaka, M., Aoki, H., and Ochiai, T. 1987. FK506, a novel immunosuppressant isolated from Streptomyces. II. Immunosuppressive effect of FK-506 in vitro. *J. Antibiotics* 40: 1256–1265.

19. Koletsky, A. J., Harding, M. W., and Handschumacher, R. E. 1986. Cyclophilin: distribution and variant properties in normal and neoplastic tissues. *J. Immunol.* 137: 1054–1059.

20. Kronke, M., Leonard, W. J., Depper, J. M. Arya, S. K., Wong-staal, F., Gallo, R. C., Waldman, T. A. and Greene, W. C. 1984. Cyclosporin A inhibits T-cell growth factor gene expression at the level of mRNA transcription. *Proc. Natl. Acad. Sci. USA* 81: 5214–5218.

21. Lang, K., Schmith, F. X. and Fisher, G. 1987. Catalysis of protein folding by prolyl isomerase. *Nature* 329: 268–270.

22. Leppert, G., McDevitt, R., Falco, S. C., Van Dyk, T. K., Ficke, M. B. and Golin, J. 1990. Cloning by gene amplification of two loci conferring multiple drug resistance in Saccharomyces. *Genetics* 125: 13–20.

23. Martel, R. R., Klicius, J., and Galet, S. 1977. Inhibition of the immune response by rapamycin, a new antifungal antibiotic. *Can. J. Physiol. Pharmacol.* 55: 48–51.

24. Metcalfe, S. M. and Richards, F. M. 1990. Cyclosporin, FK506, and Rapamycin. Some effects on early activation events in serum-free, mitogen-stimulated mouse spleen cells. *Transplantation* 49: 798–802.

25. Parent, S. A. and Thompson, J. R. (1991) Unpublished data.

26. Rothstein, R. 1983. One-step gene disruption in yeast., p. 202–211. In R. Wu, L. Grossman and K. Moldave (eds), Recombinant DNA Part C Methods in Enzymology, Vol. 101. Acadmeic Press, New York.

27. Saunders, G. W., and Rank, G. H. 1982. Allelism of pleiotropic drug resistance in *Saccharomyces cerevisiae*. *Can. J. Genet. Cytol.* 24: 493–503.

28. Sawada, S., Suzuki, G., Kawase, Y. and Takaku, F. 1987. Novel immunosuppressive agent, FK506. In vitro effects on the cloned T cell activation. *J. Immunol.* 139: 1797–1803.

29. Schneuwly, S., Shortridge, R. D., Larrivee, D. C., Ono, T., Ozaki, M., and Pak, W. L. (1989). Drosophila ninaA gene encodes an eye-specific cyclophilin (cyclosporine A binding protein). *Proc. Natl. Acad. Sci. USA* 86: 5390–5394.

30. Sherman, F., Fink, G. and Hicks, J. Laboratory course manual for Methods in Yeast Genetics. Cold Spring Harbor Laboratory. Cold Spring Harbor, N.Y. 1986.

31. Shevak, E. M. 1985. The effects of cyclosporin A on the immune system, p. 397–423. In Paul, W., Garrison Fathman, C and Metzger, H. (eds), *Ann. Rev. Immunol.*, Vol. 3. Ann. Rev. Inc., Palo Alto, Calif.

32. Shieh, B. H., Stamnes, M. A., Seavello, S., Harris, G. L. and Zuker, C. S. 1989. The ninaA gene required for visual transduction in Drosophila encodes a homologue of cyclosporin A-binding protein. *Nature*. 338: 67–70.

33. Siekierka, J. J., Staruch, M. J., Hung, S. H. Y., and Sigal, N. H. 1989. FK-506, a potent novel immunosuppressive agent, binds to a cytosolic protein which is distinct from the cyclosporin A-binding protein. *J. Immunol.* 143: 1580–1583.

34. Siekierka, J. J., Hung, S. H. Y., Poe, M., Shirley Lin, C. and Sigal, N. H. 1989. A cytosolic binding protein for the immunosuppressant FJ506 has peptidyl-prolyl isomerase activity but is distinct from cyclophilin. *Nature* 341: 755–757.

35. Siekierka, J. J., Wiederrecht, G., Greulich, H., Boulton, D., Hung, S. H. Y., Cryan, J., Hodges, P. J., and Sigal, N. H. 1990. The cytosolic-binding protein for the immunosuppressant FK-506 is both a ubiquitous and highly conserved peptidyl-prolyl cis-trans isomerase. *J. Biol. Chem.* 265: 21011–21015.

36. Sigal, N. H., Siekierka, J. J., and Dumont, F. J. 1990. Observations on the mechanism of action of FK-506. *Bioch. Pharmacol.* 40: 2201–2208.

37. Sikorski, R. S. and Hieter, P. 1989. A system shuttle vectors and yeast host strains designed for efficient manipulation of DNA in *Saccharomyces cerevisiae*. *Genetics* 122: 19–27.

38. Sprague Jr., G. F. and Herskowitz, I. 1981. Control of yeast by the mating type locus. *J. Mol. Biol.* 153: 305–321.

39. Starzl, T., Todo, S., Fung, J., Demetris, A., Venkataramman, R., and Jain, A. 1989. FK-506 for liver, kidney, and pancreas transplantation. *Lancet* 2: 1000–1004.

40. Subik, J., Ulaszewski, S., and Goffeau, A. 1986. Genetic mapping of nuclear mucidin resistance mutations in *Saccharomyces cerevisiae*. *Curr. Genet.* 10: 665–670.

41. Takahashi, N., Hayano, T. and Suzuki, M. 1989. Peptidyl-prolyl cis-trans isomerase is the cyclosporin A-binding protein cyclophilin. *Nature* 337: 473–475.

42. Tanaka, H., Kuroda, A., Marusawa, H., Hashimoto, M., Hatanaka, H., Kino, T., Goto, T. and Okuhara, M. 1987. Physicochemical properties of FK-506, a novel immunosuppressant isolated from Streptomyces tsukubaensis. *Transp. Proceed.* 19: 11–16.

43. Thomson, A. W. 1990. FK-506: How much potential? *Immunol. Today* 10: 6–9.

44. Thomson, A. W. 1990. FK-506 enters the clinic. *Immunol. Today* 11: 35–36.

45. Tocci, M. J., Matkovich, D. A., Collier, K. A., Kwok, P., Dumont, F., Lin, S., Degudicibus, S., Siekierka, J. J., Chin, J. and Hutchinsonm, N. I. 1989. The immunosuppressant FK506 selectively inhibits expression of early T cell activation genes. *J. Immunol.* 143: 718–726.

46. Tropschug, M., Nicholson, D. W., Hartl, F. U., Kohler, H., Pfanner, N., Wachter, E., and Neuper, W. 1988. Cyclosporin A-binding protein (cyclophilin) of Neurospora crassa: One gene codes for both the cytosolic and mitochondrial forms. *J. Biol. Chem.* 263: 14433–14440.

47. Tropschug, M., Barthelmess, I. B., and Neuper, W. 1989. Sensitivity to cyclosporin A is mediated by cyclophilin in Neurospora crassa and *Saccharomyces cerevisiae*. *Nature* 342: 953-955.

48. Tropschug, M., Wachter, E., Mayer, S., Schonbrunner, E. R. and Schmid, F. X. 1990. Isolation and sequence of an FK506-binding protein from N. crassa which catalyzes protein folding. *Nature* 346: 674-677.

49. Vezina, C. Kudelski, A., and Sehgal, SN. 1975. Rapamycin (AY-22,989), a new antifungal antibiotic. I. Taxonomy of the producing streptomycete and isolation of the active principle. *J. Antibiot.* 28: 721-726.

50. Wiederrecht, G., Brizuela, L., Elliston K., Sigal, N. H. and Siekierka, J. J. 1991. FKB1 encodes a nonessential FK-506-binding protein in *Saccharomyces cerevisiae* and contains a region suggesting homology to the cyclophilins. *Proc. Natl. Acad. Sci. USA*, 88: 1029-1033.

51. Yoshimura, N., Matsui, S., Hamashima, T. and Oka, T. 1989. Effect of new immunosuppressive agent, FK-506, on human lymphocyte responses in vitro. II. Inhibition of the production of IL-2 and g-IFN, but not B cell-stimulating factor. *Transplantation* 47: 356-359.

52. Brizuela, L., Chrebet, G., Bostian, K. A. and Parent, S. S. 1991. Antifungal Properties of the Immunosuppressant FK-506: Identification of an FK-506-Responsive Yeast Gene Distinct from FKB1 *Molecular and Cellular Biology*, Vol. 11, No. 9, pp. 4616-4626.

What is claimed is:

1. A biologically pure culture of *Saccharomyces cerevisiae* having all the identifying characteristics of *Saccharomyces cerevisiae* ATCC No. 74055.

* * * * *